US008998793B2

(12) United States Patent
Oatley et al.

(10) Patent No.: US 8,998,793 B2
(45) Date of Patent: Apr. 7, 2015

(54) FEEDER-FREE METHOD FOR CULTURE OF BOVINE AND PORCINE SPERMATOGONIAL STEM CELLS

(71) Applicant: Washington State University Research Foundation, Pullman, WA (US)

(72) Inventors: Jon Michael Oatley, Pullman, WA (US); Melissa Joan Oatley, Pullman, WA (US)

(73) Assignee: Washington State University, Pullman, WA (US)

( * ) Notice: Subject to any disclaimer, the term of this patent is extended or adjusted under 35 U.S.C. 154(b) by 181 days.

(21) Appl. No.: 13/763,908

(22) Filed: Feb. 11, 2013

(65) Prior Publication Data
US 2013/0211186 A1 Aug. 15, 2013

Related U.S. Application Data

(60) Provisional application No. 61/598,437, filed on Feb. 14, 2012.

(51) Int. Cl.
| | |
|---|---|
| A61B 17/43 | (2006.01) |
| C12N 5/00 | (2006.01) |
| C12N 5/076 | (2010.01) |
| C12N 5/073 | (2010.01) |
| C12N 5/071 | (2010.01) |
| C12M 1/00 | (2006.01) |
| A61K 35/52 | (2006.01) |

(Continued)

(52) U.S. Cl.
CPC .............. *C12N 5/061* (2013.01); *C12N 5/0603* (2013.01); *C12N 5/0602* (2013.01); *C12M 21/00* (2013.01); *A61K 35/52* (2013.01); *C12N 5/0656* (2013.01); *C12N 5/0683* (2013.01); *C12N 15/873* (2013.01); *C12N 2500/25* (2013.01); *C12N 2500/32* (2013.01); *C12N 2500/38* (2013.01); *C12N 2500/44* (2013.01); *C12N 2500/46* (2013.01); *C12N 2501/115* (2013.01); *C12N 2501/125* (2013.01); *C12N 2501/13* (2013.01); *C12N 2501/21* (2013.01); *C12N 2502/13* (2013.01); *C12N 2502/246* (2013.01); *C12N 2533/90* (2013.01)

(58) Field of Classification Search
CPC ........ A61B 17/435; C12N 5/00; C12N 5/061; C12N 5/0602; C12N 5/0603
USPC ....................... 600/33–35; 435/325, 404, 405
See application file for complete search history.

(56) References Cited

FOREIGN PATENT DOCUMENTS

WO WO 2013/122864 A1 8/2013

OTHER PUBLICATIONS

Aponte, Pedro M. et al., "Propagation of bovine spermatogonial stem cells in vitro" Reproduction Research, Jan. 1, 2008 vol. 136, No. 5, pp. 543-557.

(Continued)

*Primary Examiner* — John Lacyk
(74) *Attorney, Agent, or Firm* — McKee, Voorhees & Sease

(57) ABSTRACT

The present invention relates to the production and culture of undifferentiated spermatogonial stem cells that can be maintained long term and are feeder free. The resultant feeder-free populations can be used in any of a number of protocols including the generation of progeny bulls. The present invention includes novel methods required for the successful enrichment of bovine spermatogonial stem cells, novel cell lines and other components used for the same, as well as the resultant stem cell compositions.

17 Claims, 1 Drawing Sheet

(51) Int. Cl.
*C12N 5/077* (2010.01)
*C12N 15/873* (2010.01)

(56) References Cited

OTHER PUBLICATIONS

Bahadorani, M. et al., "Short-term in-vitro culture of goat enriched spermatogonial stem cells using different serum concentrations" J. Assist Reprod. Genet (2012) 29:39-46.

Goel, Sandeep et al., "Spermatogonia-specific proteins expressed in prepubertal buffalo (*Bubalus bubalis*) testis and their utilization for isolation and in vitro cultivation of spermatogonia", ScienceDirect Theriogenology 74 (2010) pp. 1221-1232.

Kanatsu-Shinohara, Mita et al., "Serum-Feeder-Free Culture of Mouse Germline Stem Cells", Biology of Reproduction 84, 97-105 (2011).

Kanatsu-Shinohara, Mita et al., "Long-Term Culture of Mouse Male Germline Stem Cells Under Serum- or Feeder-Free Conditions" Biology of Reproduction 72, 985-991 (2005).

Lim, J. J. et al., "Long-term proliferation and characterization of human spermatogonial stem cells obtained from obstructive and non-obstructive azoospermia under exogenous feeder-free culture conditions", Cell Prolif., 2010, 43, 405-417.

Talbot, Neil C. et al., "Establishment of a bovine blastocyst-derived cell line collection for the comparative analysis of embryos created in vivo and by in vitro fertilization, somatic cell nuclear transfer, or parthenogenetic activation", In vitro Cell. Dev. Biol.-Animal (2007) 43:59-71.

Yin, Jinlong et al., "In vitro myogenic and adipogenic differentiation model of genetically engineered bovine embryonic fibroblast cell lines", 2010.

Washington State University Research Foundation, PCT/US2013/025537 filed Feb. 11, 2013, Written Opinion of the International Preliminary Examining Authority mailed Jan. 29, 2014.

Losino, Noelia et al. "Maintenance of Murine Embryonic Stem Cells' Self-Renewal and Pluripotency with Increase in Proliferation Rate by a Bovine Granulosa Cell Line-Conditioned Medium", Stem Cells and Development, vol. 20. No. 8, Nov. 8, 2011, pp. 1439-1449.

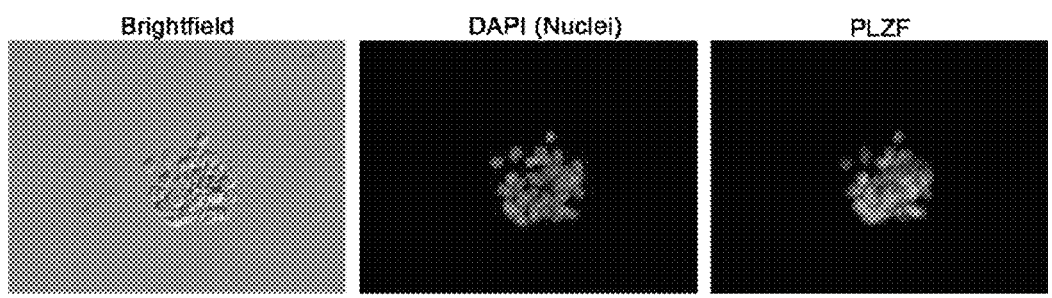

FEEDER-FREE METHOD FOR CULTURE OF BOVINE AND PORCINE SPERMATOGONIAL STEM CELLS

CROSS REFERENCE TO RELATED APPLICATION

This application claims priority under 35 U.S.C. §119 to provisional application Ser. No. 61/598,437 filed Feb. 14, 2012, herein incorporated by reference in its entirety.

GRANT REFERENCE

This invention was made with government support under Contract No. 117232-001, awarded by the United States Department of Agriculture. The government has certain rights in the invention.

BACKGROUND OF THE INVENTION

Stem cells are undifferentiated cells that possess two hallmark properties; self-renewal and the ability to differentiate into one or more different cell lineages. The process of self-renewal involves the self-replication of a stem cell to allow for propagation and expansion, wherein the stem cell remains in an undifferentiated state. Progenitor cells are also undifferentiated cells that have the ability to differentiate into one or more cell lineages, but have limited or no ability to self-renew. When maintained in culture, undifferentiated cells, such as stem or progenitor cells, can undergo spontaneous differentiation, thereby losing the desired, undifferentiated cell phenotype. Thus, culture methods that minimize spontaneous differentiation in order to maintain the undifferentiated stem or progenitor cell state are needed.

Keeping undifferentiated cells in an undifferentiated state is critical to their use, e.g., in industry and medicine, since a major scientific and therapeutic usefulness of these cells lies in their ability to expand into homogenous populations that can further proliferate or differentiate into mature cells as needed, e.g., for scientific study or to repair damage to cells or tissues of a patient. Once they have spontaneously differentiated in cell culture, the cells are less proliferative and less able to differentiate into different types of cells as needed. A homogenous culture of undifferentiated stem cells is therefore a highly sought after but unrealized goal of research scientists and industry.

Current methods for culturing undifferentiated cells (e.g., various types of stem cells) attempt to minimize such spontaneous differentiation by delivering fibroblast growth factor 2 (FGF2) to the cell cultures daily, or, less frequently than every day, which is known as "feeding". FGF2 has been shown to promote self-renewal of stem cells by inhibiting differentiation of the stem cell; however this inhibition is incomplete, and the stem cell cultures tend to gradually differentiate, thereby diminishing usefulness of the stem cell culture. Furthermore, stem cells, such as embryonic or spermatogonial stem cells, typically need to be grown on mouse embryonic fibroblast (MEF) feeder cells. This is a cumbersome step that is desirable to remove and results in a population of cells stem cells contaminated with the feeder cells that cannot be used in various fertilization protocols and production of gametes.

The ability to conditionally induce the development of stem cell lines through the process of spermatogenesis in vitro for the production of gametes would provide a long-sought-after technology for biomedical research, and animal breeding particularly if such protocols could be established for a variety of species. To date, most success has been achieved in rats and mice only, leaving larger mammals such as bovine, without such advances.

The discovery that stem cells residing within fractions of dissociated mouse and rat testis cells maintain their ability to regenerate spermatogenesis in testes of recipient mice was essential to establishing such culture systems. See Brinster et al., Proc Natl Acad Sci USA 1994; 91:11303-11307; Brinster et al., Proc Natl Acad Sci USA 1994; 91:11298-11302; Clothier et al., Nature 1996; 381:418-421; Kanatsu-Shinohara et al., Biol Reprod 2003; 69:612-616; and Nagano et al., Tissue Cell 1998; 30:389-397. The ability to isolate and experimentally manipulate these stem cells has opened new doors for research on spermatozoon development, assisted reproduction, cellular therapy and genetics. See Nagano et al., Biol Reprod 1999; 60:1429-1436; Mahanoy et al., Endocrinology 2000; 141:1273-1276; Mahato et al., Mol Cell Endocrinol 2001; 178:57-63; Ogawa et al., Nat Med 2000; 6:29-34; Shinohara et al., Proc Natl Acad Sci USA 2006; 103:13624-13628; Zhang et al., J Cell Physiol 2007; 211:149-158; Kazuki et al., Gene Ther 2008; 15:617-624; Kanatsu-Shinohara et al., Cell 2004; 119:1001-1012; Kanatsu-Shinohara et al., Proc Natl Acad Sci USA 2006; 103:8018-8023; and Nagano et al., Proc Natl Acad Sci USA 2001; 98:13090-13095. In view of this potential, protocols for isolating, propagating and genetically modifying fully functional rat and mouse spermatogonial stem cells in culture have been established. See Ryu et al., Dev Biol 2004; 274:158-170; Hamra et al., Dev Biol 2004; 269:393-410; Hamra et al., Proc Natl Acad Sci USA 2002; 99:14931-14936; Hamra et al., Methods Mol Biol 2008; 450:163-179; Hamra et al., Proc Natl Acad Sci USA 2005; 102:17430-17435; Ryu et al., Proc Natl Acad Sci USA 2005; 102:14302-14307; Orwig et al., Biol Reprod 2002; 67:874-879; and Kanatsu-Shinohara et al., Biol Reprod 2008. The mouse and rat were chosen as species for these studies due to their popularity as laboratory animal models for the study of human health and disease, and due to the lack of protocols for genetically modifying the rat germline using clonally expanded stem cells from culture. See Hamra et al., Proc Natl Acad Sci USA 2002; 99:14931-14936. Considering the many potential applications of the laboratory rat as a research model, a cost-effective and easy-to-prepare culture medium was sought in this study for the derivation and continuous proliferation of primary rat spermatogonial stem cell lines in vitro.

Despite these advances, even in the rat species, the procedure remains complex and largely unsuccessful. For example, media for long-term proliferation of rodent spermatogonial stem cells in vitro are relatively complex, expensive, time-consuming to prepare, plus are most effective when applied in combination with feeder layers of fibroblasts.

As can be seen a need exists for methods of culturing spermatogonial stem cells, particularly for larger mammals such as bovines.

SUMMARY OF THE INVENTION

The present invention comprises compositions and methods for culturing spematogonial stem cells. According to the invention, Applicants have developed a feeder-free culture system that allows for cultured spermatogonial stem cells to remain in an undifferentiated state and to remain viable in culture for long periods of time. Further aspects of the invention include procedures to isolate undifferentiated spermatogonia from testicular tissue, the identification of specific serum-free media that supports survival of undifferentiated spermatogonia in vitro, substrates for coating of plastic culture wells that undifferentiated spermatogonia adhere to, and finally Applicants have identified specific growth factors for the supplementation of feeder cell conditioned media that promotes maintenance and growth of bovine undifferentiated spermatogoinia. While the methods and examples disclose bovine cells, the invention is not so limited and is applicable to all livestock species including porcine.

According to the invention, Applicants have identified specific proprietary cell lines including a bovine embryonic fibroblast cell line, and a bovine somatic cell line isolated from bovine testis. These specific cell lines are used as feeder support cells to condition culture media prior to cultivation of any SSCs. The pre-cultivation technique allows for feeder free cultivation enabling the generation of pure populations of putative bovine SSCs for transplant or other uses. Applicants' cultured cells are free from contamination with other feeder cell lines and their deleterious effects, including potential host immune response, limited colonizing ability, and eventual differentiation over time.

In an embodiment, the present invention features a method of isolating undifferentiated spermatogonia, of which spermatogonial stem cells (SSCs) are a component, from testicular tissue containing at least one SSC. The method includes obtaining bovine testicular tissue which includes at least one SSC, contacting said tissue with collagenase, separating seminiferous tubules from other cell types, and thereafter contacting said seminiferous tubules with trypsin to yield a cell suspension enriched in spermatogonia and Sertoli cells. The method may also be applied to SSCs generated from induced pluripotent stem cells or even embryonic stem cells that have been manipulated to be SSCs.

In another embodiment, the invention features a method of enriching and maintaining a pure culture of undifferentiated spermatogonial cells containing at least one SSC, wherein the method includes providing a specific serum-free media with serum replacement, further providing culture cell wells that are pre-coated with Matrigel, and adding specific growth factors of GDNF, FGF2, SDF-1, and CSF-1 to pre-conditioned media all work together to provide for the first time a feeder-free culture of spermatogonial cells, preferably bovine spermatogonial cells.

In an embodiment, the invention also features a putative population of spermatogonial stem cells that remains undifferentiated, possesses the capacity for self-renewal and differentiation, is viable in culture, and is essentially pure, namely feeder-free.

In another embodiment the invention includes novel support cell lines which have been developed and which allow for the pre-conditioning of media to provide for the feeder free culture method. The cell lines include cell line bovine embryonic fibroblast 1 (or BEF1, previously BEF) derived from a 35 day old male Holstein fetus, and the second, cell lines bovine somatic cell 1 (or BSC1, previously BSC) derived from somatic cells isolated from the testis of a 4 month old Holstein bull. Together these cell lines may be used to pre-incubate culture media and will provide necessary secreted soluble factors for survival and proliferation of SSCs without the addition of feeder cells once the SSC have been introduced. According to the invention the media is first pre-conditioned with these cells and after a sufficient period of time, the feeder precondition cells are removed so that SSC cells may then be cultured.

In one aspect of the invention, the SSC is a bovine SSC. In another aspect, an SSC is derived from an organism selected from the group consisting of a mouse, a rat, a monkey, a baboon, a human, a pig and a dog.

In another aspect of the invention, cells are derived from any source of spermatogonial stem cells including a source selected from the group consisting of wild type adult testis, calf or pup testis, neonate testis, and cryptorchid adult testis.

In another aspect of the invention the cells are derived from induced pluripotent stem cells or embryonic stem cells to become spermatogonial stem cells, which then may become a source of the same used according to the invention.

In another embodiment, the invention features a feeder-free culture system for support of SSC maintenance, the system comprising enriched SSCs, serum-free defined culture medium, and media preconditioned with feeder cells. In another embodiment, the invention features a feeder-free culture system for support of SSC proliferation comprising at least one SSC, serum-free defined culture medium with serum replacement supplement (StemPro), and which has been preconditioned with the proprietary fibroblast cell line BEF1 and proprietary BSC1 feeder cells.

In one aspect of the invention, a culture system further comprises growth factors of GDNF, FGF2, SDF-1, and CSF-1. In another aspect, a culture medium comprises at least one medium selected from the group consisting of Dulbecco's MEM: Ham's Nutrient Mixture F-12 (DMEM/F12) and StemPro serum replacement supplement.

In another aspect of the invention, a culture system further comprises growth plastic culture wells that are pre-coated with a commercially available matrix such as Matrigel (growth factor reduced version). Without such coating the cells do not attach to the plastic well and cannot be maintained long-term in culture.

In another embodiment, the invention features a composition comprising a population of pure, enriched SSCs, wherein the enriched population of SSCs is free of embryonic fibroblast cells or other types of feeder cells.

In another embodiment, the invention features a composition comprising a population of enriched SSCs which express a specific marker of undifferentiated spermatogonia and a morphology that is similar to that of cultured SSC cells. In one aspect, the population of SSCs is substantially homogeneous for SSCs.

In yet another embodiment, the invention features a method of generating at least one mammalian progeny, comprising administering a population of feeder free SSCs to a testis of a male recipient mammal, allowing the enriched SSCs to generate a colony of spermatogenesis in the recipient mammal, and mating the recipient mammal with a female mammal of the same species as the recipient mammal. In one aspect, a population of enriched SSCs is administered to the lumen of a seminiferous tubule of the recipient mammal. In another aspect, the recipient mammal is infertile.

In an embodiment of the invention, a recipient mammal is selected from the group consisting of a rodent, a primate, a dog, a bovine, a pig and a human. In another embodiment, a rodent is selected from the group consisting of a mouse and a rat. In yet another aspect, the primate is a baboon.

In another embodiment, the invention features a kit for maintaining at least one SSC in a feeder-free culture system. The kit includes a culture system comprising serum-free defined culture medium, proprietary BSC1 and BEF1 cells for pre-conditioning culture medium, (or medium that has already been preconditioned with the same), an applicator, and instructional material, wherein the instructional material comprises instructions for the use of the kit to maintain at least one SSC in the feeder-free culture system.

In an embodiment, the invention features a progeny animal produced according to a method of the invention. In another embodiment, the invention features a progeny animal made according to a method of the invention, wherein the enriched SSCs used to make the progeny animal contain at least one genetic mutation. In one aspect, a genetic mutation is created using recombinant techniques.

The claimed invention comprehends, in part, using certain naturally occurring or transgenically generated ("genetically") male-sterile bovines as recipients for donor spermatogonial stem cells with which the animals also are immuno-compatible. Accordingly, the transplanted spermatogonial stem cells are free to develop into functional spermatozoa and to fertilize females in the absence of competition from sperm that also would be produced were the recipient male fertile. In this manner, 100% germline transmission of the donor cell haplotype can be achieved from a relatively low number of transplanted sperm stem cells.

Thus, pursuant to one aspect of the present invention, a methodology is provided for effecting germline transmission of a donor haplotype. The inventive method comprises the steps of (A) providing cells of a spermatogonial stem cell line that is derived from mammal testes, from induced pluripotent stem cells, or embryoiniuc stem cells, which cell line embodies a predetermined genetic background, and then (B) transplanting one or more of the cells into a male-sterile recipient, such that transplanted cells develop into fertilization-competent, haploid male gametes.

In accordance with another aspect of the invention, a library is provided of cells of a spermatogonial stem cell line that is derived from mammal testes, or from induced pluripotent stem cells, or embryoiniuc stem cells. A library of the invention contains a plurality of gene knockout or "knockin" mutant stem cells.

DESCRIPTION OF THE FIGURES

FIG. 1 shows the Maintenance of bovine undifferentiated spermatogonia in feeder-free culture. Left image is representative of a germ cell clump formed during feeder-free culture on Matrigel coated culture wells with BEF1 conditioned media. The middle image is the clumps stained with DAPI to label nuclei of individual cells. The right image is immunostaining for the undifferentiated spermatogonial marker PLZF.

DETAILED DESCRIPTION OF THE INVENTION

Unless otherwise defined herein, scientific and technical terms used in connection with the invention shall have the meanings that are commonly understood by those of ordinary skill in the art. Further, unless otherwise required by context, singular terms shall include the plural and plural terms shall include the singular. Generally, nomenclatures used in connection with, and techniques of, biochemistry, enzymology, molecular and cellular biology, microbiology, genetics and protein and nucleic acid chemistry and hybridization described herein are those well known and commonly used in the art. The methods and techniques are generally performed according to conventional methods well known in the art and as described in various general and more specific references that are cited and discussed throughout the present specification unless otherwise indicated. See, e.g., Sambrook et al. Molecular Cloning: A Laboratory Manual, 2d ed., Cold Spring Harbor Laboratory Press, Cold Spring Harbor, N.Y. (1989); Ausubel et al., Current Protocols in Molecular Biology, Greene Publishing Associates (1992, and Supplements to 2002); Harlow and Lane, Antibodies: A Laboratory Manual, Cold Spring Harbor Laboratory Press, Cold Spring Harbor, N.Y. (1990); Taylor and Drickamer, Introduction to Glycobiology, Oxford Univ. Press (2003); Worthington Enzyme Manual, Worthington Biochemical Corp., Freehold, N.J.; Handbook of Biochemistry: Section A Proteins, Vol. I, CRC Press (1976); Handbook of Biochemistry: Section A Proteins, Vol. II, CRC Press (1976); Essentials of Glycobiology, Cold Spring Harbor Laboratory Press (1999).

The following terms, unless otherwise indicated, shall be understood to have the following meanings.

The phrase "spermatogonial stem cells" in this description denotes stem cells either isolated from the testis, created from induced pluripotent stem cells, from embryonic stem cells or any other method to obtain such cells. For example, mammalian induced pluripotent stem cells created from skin cells have been used to create germ cells. See, Easley CA 4$^{th}$ et al, Cell Rep. 2012 Sep. 27; 2(3):440-6, "Direct differentiation of human pluripotent stem cells into haploid spermatogenic cells". Spermatogonial stem cells are incapable of fertilizing an egg cell but can give rise to cells that develop into sperm and so produce viable offspring. Isolated spermatogonial stem cells can be cultured for a prolonged time period without losing their properties and can efficiently repopulate the testes of suitable recipient male animals described, for instance, in Oatley J. M. et al., Methods Enzymol. 419:259 (2006).

The articles "a" and "an" are used herein to refer to one or to more than one (i.e., to at least one) of the grammatical object of the article. By way of example, "an element" means one element or more than one element.

As used herein, the terms "gene" and "recombinant gene" refer to nucleic acid molecules comprising an open reading frame encoding a polypeptide. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the invention.

Moreover, nucleic acid molecules encoding proteins from other species (homologs), which have a nucleotide sequence which differs from that of the proteins described herein are within the scope of the invention. Nucleic acid molecules corresponding to natural allelic variants and homologs of a cDNA of the invention can be isolated based on their identity to nucleic acid molecules using the human cDNAs, or a portion thereof, as a hybridization probe according to standard hybridization techniques under stringent hybridization conditions.

As the term is used herein, "modulation" of a biological process refers to the alteration of the normal course of the biological process. For example, modulation of the activity of a spermatogonial stem cell may be an increase in the activity of the cell. Alternatively, modulation of the activity of a spermatogonial stem cell may be a decrease in the activity of the cell.

"Enriching," as the term is used herein, refers to the process by which the concentration, number, or activity of something is increased from a prior state. For example, a population of 100 spermatogonial stem cells is considered to be "enriched" in spermatogonial stem cells if the population previously contained only 50 spermatogonial stem cells. Similarly, a population of 100 spermatogonial stem cells is also considered to be "enriched" in spermatogonial stem cells if the population previously contained 99 spermatogonial stem cells. Likewise, a population of 100 spermatogonial stem cells is also considered to be "enriched" in spermatogonial stem cells even if the population previously contained zero spermatogonial stem cells.

As the term is used herein, "population" refers to two or more cells.

As the term is used herein, "substantially separated from" or "substantially separating" refers to the characteristic of a population of first substances being removed from the proximity of a population of second substances, wherein the population of first substances is not necessarily devoid of the second substance, and the population of second substances is not necessarily devoid of the first substance. However, a population of first substances that is "substantially separated from" a population of second substances has a measurably lower content of second substances as compared to the non-separated mixture of first and second substances.

In one aspect, a first substance is substantially separated from a second substance if the ratio of the concentration of the first substance to the concentration of the second substance is greater than about 1. In another aspect, a first substance is substantially separated from a second substance if the ratio of the concentration of the first substance to the concentration of the second substance is greater than about 2. In yet another aspect, a first substance is substantially separated from a second substance if the ratio of the concentration of the first substance to the concentration of the second substance is greater than about 5. In another aspect, a first substance is substantially separated from a second substance if the ratio of the concentration of the first substance to the concentration of the second substance is greater than about 10. In still another aspect, a first substance is substantially separated from a second substance if the ratio of the concentration of the first substance to the concentration of the second substance is greater than about 50. In another aspect, a first substance is substantially separated from a second substance if the ratio of the concentration of the first substance to the concentration of the second substance is greater than about 100. In still another aspect, a first substance is substantially separated from a second substance if there is no detectable level of the second substance in the composition containing the first substance.

"Substantially homogeneous," as the term is used herein, refers to a population of a substance that is comprised primarily of that substance, and one in which impurities have been minimized.

"Maintenance" of a cell or a population of cells refers to the condition in which a living cell or living cell population is neither increasing nor decreasing in total number of cells in a culture. Alternatively, "proliferation" of a cell or population of cells, as the term is used herein, refers to the condition in which the number of living cells increases as a function of time with respect to the original number of cells in the culture.

A "defined culture medium" as the term is used herein refers to a cell culture medium with a known composition.

By the term "applicator" as the term is used herein, is meant any device including, but not limited to, a hypodermic syringe, a pipette, a bronchoscope, a nebulizer, and the like, for administering a composition of the invention to a mammal.

As used herein, an "instructional material" includes a publication, a recording, a diagram, or any other medium of expression which can be used to communicate the usefulness of a method and/or composition of the invention in a kit for maintaining, proliferating, or administering any composition recited herein. The instructional material of the kit of the invention may, for example, be affixed to a container which contains a composition of the invention or may be shipped together with a container which contains a composition. Alternatively, the instructional material may be shipped separately from the container with the intention that the instructional material and the compound be used cooperatively by the recipient.

As the term is used herein, a cell is said to be "eliminated" from a population of cells, or from a culture medium, when the cell no longer exerts one or more of a physical, biological or chemical effect on the population of cells or culture medium. For example, a cell may be eliminated from a culture medium by physically removing the cell using FACS or by using an antibody specific for a cell surface marker unique to that cell. A cell may also be eliminated from a culture medium by rendering the biological activity of that cell inert, such as, for example, by using a neutralizing antibody that is specific for that cell.

A cell is "essentially eliminated" from a population of cells, or from a culture medium, when most, but not all of the total number of such cells no longer exerts one or more of a physical, biological or chemical effect on the population of cells or culture medium. For example, a particular type of cell may be essentially eliminated from a culture medium if at least 75% of the cells of that type are removed from the culture medium by using an antibody specific for a cell surface marker unique to that cell. More preferably, at least 80% of the cells are eliminated from the culture medium, even more preferably, at least 85%, more preferably, at least 90%, and even more preferably, at least 95% of the cells are eliminated from the culture medium.

A cell is a "testis-derived" cell, as the term is used herein, if the cell is derived from a testis. By way of a non-limiting example, testis-derived cells include a spermatogonial stem cell, a somatic cell, and a germ cell.

Methods of Enriching Spermatogonial Stem Cells

The present invention features a method of enriching spermatogonial stem cells (SSCs). It has been shown for the first time herein that, SSCs may be cultured in a feeder free protocol with long term survival to enrich a population of cells. In one embodiment of the invention, an SSC is obtained from a bovine. Stem cell enrichment is useful for various purposes in the field of medical treatment, diagnosis and research, including stem-cell based therapies for repopulation of the cells in an organism, as well as laboratory research to identify growth factors responsible for control of the maintenance and proliferation of stem cells as well as for artificial insemination.

The present invention comprises compositions and methods for culturing spematogonial stem cells. According to the invention, Applicants have developed a feeder free culture system that allows for isolated (or otherwise obtained) bovine spermatogonial stem cells to remain in an undifferentiated state and to remain viable in culture for long periods of time. Induced pluripotent stem cells or embryonic stem cells could also be used. Further aspects of the invention include procedures to isolate undifferentiated spermatogonia from bovine testicular tissue, the identification of specific serum-free media that supports survival of bovine undifferentiated spermatogonia in vitro, substrates for coating of plastic culture wells that cultured bovine undifferentiated spermatogonia adhere to, and finally Applicants have identified specific growth factors for the supplementation of feeder cell conditioned media that promotes maintenance and growth of bovine undifferentiated spermatogoinia.

According to the invention, Applicants have identified specific proprietary cell lines including a fibroblast bovine embryonic cell line, and a bovine somatic cell line isolated from bovine testis or otherwise obtained. These specific cell lines are used as feeder support cells to condition culture media prior to cultivation of any SSCs. The pre-cultivation technique allows for feeder free cultivation enabling the generation of pure populations of bovine spermatogonial SSCs for transplant or other uses without contamination from other feeder cell lines and their deleterious effects including potential host immune response, limiting the colonizing ability of the SSCs.

In an embodiment, the present invention features a method of isolating spermatogonial stem cells (SSCs) from bovine testicular tissue containing at least one SSC. The method includes obtaining bovine testicular tissue which includes at least one SSC, contacting said tissue with collagenase, separating seminiferous tubules from other cell types, and thereafter contacting said seminiferous tubules with trypsin to yield a cell suspension enriched in spermatogonia and Sertoli cells.

In another embodiment, the invention features a method of enriching and maintaining a pure culture of spermatogonial stem cells (SSCs) from a population of testis-derived, induced pluripotent stem cells, or embryonic stem cells containing at least one SSC, wherein the method includes providing a specific serum-free media with serum replacement, further providing culture cell wells that are pre-coated with Matrigel, and adding specific growth factors of GDNF, FGF2, SDF-1, and CSF-1 to pre-conditioned media all work together to provide for the first time a feeder-free culture of spermatogonial cells, preferably bovine spermatogonial cells.

In an embodiment, the invention also features a population of spermatogonial stem cells that remains undifferentiated, possessing the capacity for self-renewal and differentiation, is viable in culture, and is essentially pure, namely feeder-free.

In another embodiment the invention includes novel support cell lines which have been developed and which allow for the pre-conditioning of media to provide a feeder free culture method. The cell lines include cell line BEF1 derived from a 35 day old male Holstein fetus, and the second, cell lines BSC1 derived from somatic cells isolated from the testis of a 4 month old Holstein bull. Together these cell lines may be used to pre-incubate culture media and will provide necessary secretion factors for survival and proliferation of SSCs without the addition of feeder cells to the incubating SSCs.

In one aspect of the invention, an SSC is a bovine SSC. In another aspect, an SSC is derived from an organism selected from the group consisting of a mouse, a rat, a monkey, a baboon, a human, a pig and a dog.

In another aspect of the invention, cells are derived from a source selected from the group consisting of wild type adult testis, pup testis, neonate testis, induced pluripotent cells, embryonic stem cells, and/or cryptorchid adult testis.

In an embodiment, the invention features a serum-free culture system for support of SSC maintenance, the system comprising enriched SSCs, serum-free defined culture medium, and media preconditioned with feeder cells. In another embodiment, the invention features a serum-free culture system for support of SSC proliferation comprising at least one SSC, serum-free defined culture medium with serum replacement supplement (StemPro), and which has been preconditioned with the proprietary fibroblast cell line BEF1 and proprietary BSC1 feeder cells.

In one aspect of the invention, a culture system further comprises growth factors of GDNF, FGF2, SDF-1, and CSF-1. In another aspect, a culture medium comprises at least one medium selected from the group consisting of Dulbecco's MEM: Ham's Nutrient Mixture F-12 (DMEM/F12) and StemPro serum replacement supplement.

In another aspect of the invention, a culture system further comprises growth plastic culture wells that are pre-coated with a commercially available matrix such as Matrigel (growth factor reduced version). Without such coating the cells do not attach to the plastic well and cannot be maintained long-term in culture.

In an embodiment, the invention features a composition comprising a population of pure, enriched SSCs, wherein the enriched population of SSCs is free of embryonic fibroblast cells or other types of feeder cells.

In another embodiment, the invention features a composition comprising a population of enriched SSCs which express a specific marker of undifferentiated spermatogonia and a morphology that is similar to that of cultured SSC cells. In one aspect, a population of SSCs is substantially homogeneous for SSCs.

In an embodiment, the invention features a method of generating at least one mammalian progeny, comprising administering a population of feeder free SSCs to a testis of a male recipient mammal, allowing the enriched SSCs to generate a colony of spermatogenesis in the recipient mammal, and mating the recipient mammal with a female mammal of the same species as the recipient mammal. In one aspect, a population of enriched SSCs is administered to the lumen of a seminiferous tubule of the recipient mammal. In another aspect, the recipient mammal is infertile.

In an embodiment of the invention, a recipient mammal is selected from the group consisting of a rodent, a primate, a dog, a bovine, a pig and a human. In another embodiment, a rodent is selected from the group consisting of a mouse and a rat. In yet another aspect, the primate is a baboon.

In one embodiment, the invention features a method of generating at least one progeny mammal, comprising administering a population of feeder free enriched SSCs to a testis of a male recipient mammal, allowing the enriched SSCs to generate a colony of spermatogenic cells in the recipient mammal, and mating the recipient mammal with a female mammal of the same species as the recipient mammal.

In another embodiment, the invention features a kit for maintaining at least one SSC in a feeder-free culture system. The kit includes a culture system comprising serum-free defined culture medium, proprietary BSC1 and BEF1 cells for pre-conditioning culture medium, an applicator, and instructional material, wherein the instructional material comprises instructions for the use of the kit to maintain at least one SSC in the feeder-free culture system.

In an embodiment, the invention features a progeny animal produced according to a method of the invention. In another embodiment, the invention features a progeny animal made according to a method of the invention, wherein the enriched SSCs used to make the progeny animal contain at least one genetic mutation. In one aspect, a genetic mutation is created using recombinant techniques.

The claimed invention comprehends, in part, using certain naturally occurring or transgenically generated ("genetically") male-sterile bovines as recipients for donor sperm stem cells with which the animals also are immuno-compatible. Spermatogenesis in these animals is severely disrupted. Accordingly, the transplanted sperm stem cells are free to develop into functional spermatozoa and to fertilize females in the absence of competition from sperm that also would be produced were the recipients male-fertile. In this manner, 100% germline transmission of the donor cell haplotype can be achieved from a relatively low number of transplanted sperm stem cells.

Thus, pursuant to one aspect of the present invention, a methodology is provided for effecting germline transmission of a donor haplotype. The inventive method comprises the steps of (A) providing cells of a spermatogonial stem cell line that is derived from mammal testes, from induced pluripotent stem cells, or created from embryonic stem cells which cell line embodies a predetermined genetic background, and then (B) transplanting one or more of the cells into a male-sterile recipient, such that transplanted cells develop into fertilization-competent, haploid male gametes.

In accordance with another aspect of the invention, a library is provided of cells of a spermatogonial stem cell line that is derived from mammal testes, induced from pluripotent stem cells, or created from embryonic stem cells. A library of the invention contains a plurality of gene knockout or "knockin" mutant stem cells.

In accordance with an additional aspect of the invention, a medium for growing spermatogonial stem cells is provided, in addition to methods for culturing spermatogonial stem cells.

Feeder-Free Spermatogonial Stem Cell Culture Systems

The present invention features a feeder-free culture system for the in vitro maintenance and proliferation of SSCs. This is because it has been shown herein for the first time that bovine undifferentiated spermatogonia, of which SSCs are a component of, can be maintained and proliferated in media that has been pre-conditioned with feeder cells, but that does not contain feeder cells in vitro. By way of the present invention, a culture system having minimal, defined conditions has been established for the in vitro culturing of bovine SSCs, which system provides the ability investigate SSC biology in a defined way, as well as the ability to identify individual factors required for maintenance and expansion of SSCs. In a preferred embodiment, the feeder free culture method allows for generation of a population of SSC cells that is free from contamination by feeder cells for use in in vitro fertilization and other aspects of commercial bovine production.

In one embodiment of the invention, a feeder-free SSC culture system includes a preconditioned feeder medium. In one aspect of the invention, the preconditioning feeder cells are Applicants' proprietary cell lines including the bovine embryonic fibroblast lines BEF1 and the bovine somatic cell line BSC1. In another aspect of the invention, the preconditioning feeder cells can include, but are not limited to, elements derived from these lines, including cells, components thereof, and the like.

Applicants have identified a critical medium for culture of the SSCs. This in one aspect of the invention, the medium for culture and preconditioning is a serum-free defined medium includes minimal essential medium-α (MEMα). In another aspect of the invention, the serum-free defined medium includes Ham's F10 culture medium. In yet another aspect of the invention, the serum-free defined medium is Dulbecco's MEM: Ham's Nutrient Mixture F-12 (DMEM/F12). As will be understood by the skilled artisan when armed with the present disclosure, a serum-free defined medium of the present invention also includes a mixture of two or more media wherein one of which is DMEM/F12.

Therefore, the present invention includes a composition including a defined medium that has been preconditioned with one or more feeder cell lines for the maintenance or proliferation of SSCs. As will be understood based on the disclosure set forth herein, a culture system of the invention is useful for the maintenance or expansion of SSCs. In one aspect of the invention, SSCs useful in the culture system are SSCs enriched using the methods or compositions of the present invention. In another aspect, SSCs useful in the culture system are SSCs that have not been previously enriched according to the methods or compositions of the present invention.

In one embodiment of the invention, a feeder-free defined medium further includes SSCs. The skilled artisan will understand, in view of the present disclosure, that SSCs from any source may be maintained or expanded using the feeder-free culture system of the invention. That is, SSCs obtained from a population of testis-derived cells can be obtained from testis cells derived from any mammalian source including, but not limited to, human testis, rat testis, mouse testis, and preferably, cow or bovine testes. Sources of SSCs further include wild type adult testis, induced pluripotent stem cells, embryonic stem cells, adult testis having one or more genetic mutations, juvenile testis, neonate testis, and/or cryptorchid adult testis. Methods for introduction of genetic mutations to the DNA in a cell, such as an SSC, are well-known in the art and will not be discussed further herein.

It will also be understood, based on the disclosure set forth herein, that a sterile male can be a source for SSCs. Therefore, another aspect of the invention includes a sterile male as a source of SSCs of the present invention.

As described in detail elsewhere herein, the basic feeder-free defined medium of the present invention may further include any components known by the skilled artisan to be useful in the culturing of cells. In one embodiment, a feeder-free defined medium includes at least one growth factor. Growth factors useful in the present invention include, but are not limited to, stem cell factor (including mouse SCF), glial cell line-derived neurotrophic factor (GDNF), GDNF-family receptor (including GFR.alpha.1), leukemia inhibitory factor (LIF), basic fibroblast growth factor (including human bFGF), acidic fibroblast growth factor (aFGF), colony stimulating factor (CSF), stromal derived factor 1 (SDF-1), epidermal growth factor (EGF), insulin-like growth factor (including IGF-I), platelet-derived growth factor (PDGF), and transforming growth factor (including TGF-β I through III, as well as the TGF β. superfamily BMP-1 through 12, GDF 1 through 8, dpp, 60A, BIP, OF). In a preferred embodiment the growth factors include GDNF, FGF2, and CSF-1.

The present invention therefore also includes methods of maintaining or proliferating SSCs in a feeder-free defined culture medium. In one embodiment, the invention features a method of maintaining SSCs in a feeder-free culture system. The method includes providing at least one SSC in a feeder-free culture system as defined in detail elsewhere herein.

An SSC may be identified as being "maintained" in the feeder-free defined culture system by assessing the activity of an SSC at various time points in the culture medium and comparing the activity with the activity of the SSCs at the start of the culture period. As will be understood by the skilled artisan, little or no loss of activity is an indication that SSCs have been maintained in culture. Methods of measuring the activity of SSCs are described in detail elsewhere herein.

In another embodiment, the invention features a method of proliferating SSCs in a feeder-free culture system. The method includes providing at least one SSC in a feeder-free culture system as defined in detail elsewhere herein. A SSC may be identified as being "proliferated" in the feeder-free defined culture system by assessing the SSC activity at various time points in the culturing process and comparing the activity with the activity of the SSC at the start of the culture period. An increase in the activity between the start of the culture period and any later time point is an indication that SSCs have been proliferated. Methods of measuring the activity of SSCs are described in detail elsewhere herein. SSCs that can be proliferated according to the present invention include, but are not limited to, bovine SSC, human SSC, mouse SSC and rat SSC.

Additionally, the degree of proliferation of SSCs in a feeder-free culture system of the present invention may be assessed by counting the number of cells present at a specific point in time during SSC cell culture and comparing the value to the number of cells present at the start of the culture period. Based on the disclosure set forth herein, the skilled artisan will understand that these and other methods of assessing SSC maintenance and proliferation may be used. These methods include, but are not limited to, FACS and MACS.

Transplantation of Spermatogonial Stem Cells

In one aspect of the invention, one or more SSCs can be transplanted into a recipient testis. Transplantation methods are generally known in the art, and will not be discussed in extensive detail herein. For general cell transplantation methods involving the testis, see Kanatsu-Shinohara et al. (PNAS, 99:1383-1388 (2002)), Brinster (I) (U.S. Pat. No. 6,215,039), and Brinster (II) (U.S. Pat. No. 5,858,354), all of which are hereby incorporated by reference herein in their entirety. Brinster (I) and (II) demonstrate, in part, that SSCs transplanted from a donor to an immunologically tolerant mouse or other compatible recipient will replicate and be maintained in the recipient. The feeder free system is a great advance over traditional feeder systems in that for these to be transplanted the feeder cells have to be removed. Applicants' culture, being feeder-cell free, does not require this laborious and difficult step.

In an embodiment of the invention, one or more SSCs are introduced into the tubules of a testis. For example, a recipient male mammal can be anesthetized and the testis (or testes) surgically exposed. In one embodiment, using micromanipulation methods, a thin glass needle is introduced into exposed tubules, one after another, and each tubule is injected with a solution containing the primitive cells being used to colonize the tubule. In another embodiment, one or more SSCs can also be introduced by injecting them into other parts of the tubular system, e.g. the lumen of the rete testes. As will be understood by the skilled artisan, injection methods are available that minimize the number of injection sites and increase the efficiency of injection of SSCs into a recipient male.

A cell suspension of one or more SSCs for injection can comprise an injection medium and at least one SSC at a suitable concentration. By way of a non-limiting example, the injection medium can comprise one or more of NaCl, $Na_2HPO_4$, KCl, $KH_2PO_4$, EDTA, pyruvate, lactate, glutamine, glucose, bovine serum albumin, and DNAse I. The pH of the injection media is suitably in the range of 7.0-7.7, but as will be understood by the skilled artisan, can be adjusted to be more basic or more acidic depending upon the medium composition, the cell type and/or concentration, and the microenvironment of the recipient injection site.

In another embodiment of the invention, other systems can be used for the introduction of one or more SSCs into a recipient male. These include injection into the vas deferens and epididymis or manipulations on fetal or juvenile testes, techniques to sever the seminiferous tubules inside the testicular covering, with minimal trauma, which allow injected cells to enter the cut ends of the tubules. Alternatively neonatal testis (or testes), which are still undergoing development, can be used.

As set forth elsewhere herein, SSCs entering the testicular tubule are generally protected from destruction by the immunologically privileged environment of the internal lumen of the tubule. Cells that leak from the tubule are typically destroyed by the immune system of the host since the cells are foreign to the animal.

In another embodiment of the invention, animal strains are used which are from different species to provide donor cells (xenogeneic transfer). Sources of SSCs include, but are not limited to human, rodent, including rat and mouse, primate, including baboon, cow and dog.

The present invention is applicable to any species of animals, including humans, in which the male has testes, including but not limited to non-human transgenic animals. The invention is also not limited to mammalian species. It can be used to provide animals and animal lines of many types with a single, or many, novel genetic modification(s) or novel characteristic(s). The animals to which the present invention can be applied include humans, non-human primates (e.g., monkeys, baboons), laboratory animals, such as rodents (e.g., mice, rats, etc.), companion animals (e.g., dogs, cats), birds (such as chickens and turkeys), wild animals (e.g., buffalo, wolves), endangered animals (e.g., elephants, leopards), and zoo species (such as tigers, zebras, lions, pandas, giraffes, polar bears, monkeys, sea otters, etc.) which can be modified to permit their use in cellular diagnosis or assays. The present invention may also be advantageously applied to farm animals, including domesticated ruminants and fowl (e.g., cattle, chickens, turkeys, horses, swine, etc.), to imbue these animals with advantageous genetic modification(s) or characteristic(s).

In another embodiment of the invention, the donor and recipient mammal can be the same mammal. In one aspect, a population of cells comprising SSCs are collected from a mammal prior to destruction of the germ cell population and then reintroduced thereafter. This embodiment would preserve the ability of the mammal to reproduce following radiation therapy, for example which may be necessary during the treatment of cancer. Alternatively, spermatogonial stem cells may be harvested from the mammal and kept in culture or frozen. In this aspect of the invention, when progeny are desired, the stem cells are transplanted to a recipient testis. The donor mammal egg can then be fertilized by spermatozoa developed in the recipient testis. There are no time constraints on this procedure since the stem cells continually undergo self-renewal.

Methods of fertilization of eggs and progeny are known in the art, and will not be discussed in detail herein. By way of a non-limiting example, methods of fertilizing eggs include, but are not limited to, intracytoplasmic sperm injection (ICSI), round spermatid injection (ROSI), and the like. Additionally, by way of a non-limiting example, methods of fertilizing progeny include, but are not limited to, ICSI, ROSI, and the like.

Once an initial fertilization event is achieved and the resulting offspring is fertile, the mammal line with its novel genetic modification or characteristic is established where the novel genetic modification or characteristic is present in both male and female offspring. Thus, in accordance with the invention, a mammal may be produced harboring, in its testes only, a biologically functional germ cell which is not native to that mammal by repopulating its testicular seminiferous tubules. This (parent) mammal can produce progeny. Every cell in the progeny is genetically non-native as compared to the parent mammal.

Both the parent mammal and its progeny provided by the present invention have multiple and varied uses, including, but not limited to, uses in agriculture and biomedicine, including human gene therapy. An illustrative agricultural use of the present invention relates to increasing the breeding potential of a valuable stud animal. In another aspect of the present invention, chimeric animals useful in either biomedicine or agriculture are provided. As will be understood by the skilled artisan, when armed with the present application, the present invention provides an advantageous complementation to existing transgenic animal techniques.

The present invention alleviates the present difficulty and expense of embryological transgenic work. In one embodiment of the present invention, spermatogonial stem cells can be genetically modified and then transferred to recipient testes. The valuable genetic traits present in the resultant germ cells can be passed onto the (transgenic) progeny of the recipient stud. This particular application of the present invention is important for the genetic engineering of large agricultural animals.

As set forth herein, the present invention also has applications in gene therapy, including human gene therapy. By way of a non-limiting example, a patient with a deleterious genetic trait could undergo a testicular biopsy. Stem cells can be genetically modified to correct the deleterious trait. The patient then undergoes a treatment to remove the remaining germ cells from his testes, for example by specific irradiation of the testes. His testes (now devoid of germ cells) can then be recolonized by his own, genetically-corrected, stem cells. The patient can then father progeny free from the worry that he would pass on a genetic disease to his progeny. Alternatively, the stem cells with the corrected gene can be transplanted to a mouse and the resulting sperm used for fertilizing eggs, thereby foregoing the need for reimplanting stem cells into the original human testis.

In another embodiment, the present invention also has applications in establishing, restoring or otherwise enhancing fertility in a male mammal, including, but not limited to, humans. By way of a non-limiting example, a patient having a disease or disorder treatable by radioisotope therapy, chemotherapy, or both, is a donor of one or more SSC. After the patient has undergone radioisotope therapy, chemotherapy, or both, the patient may possibly be rendered devoid of SSC, or may be otherwise rendered infertile. By using, preparing or transplanting one or more of the patient's SSC according to the present invention, fertility in the patient may be established, restored, or otherwise enhanced.

Sterile Testes Complementation

Currently, specific causes of infertility in men remain a mystery in 40-60% of cases. See Bhasin et al., J Clin Endocrinol Metab 79, 1525-9 (1994); Sadeghi-Nejad et al., Urol J 4, 192-206 (2007); and Matzuk et al., Nat Med 14, 1197-213 (2008). In total, >5% of the male population is infertile, and >1% of all males are inflicted with a severe defect in sperm production termed azoospermia. See Bhasin et al., J Clin Endocrinol Metab 79, 1525-9 (1994); Sadeghi-Nejad et al., Urol J 4, 192-206 (2007); Barthold et al. J Urol 170, 2396-401 (2003); and Bleyer, W. A. CA Cancer J Clin 40, 355-67 (1990). Fundamentally, because azoospermia results in an inability to reproduce by natural mating, it seems enigmatic as to why this disease remains so prevalent in the human population. Such an epidemiological trend clearly points to the existence of potent environmental factors that disrupt the process of sperm production (i.e. spermatogenesis) or a substantial number of de novo mutations that could arise during a lifetime to render one sterile, but otherwise healthy. See Bhasin et al., J Clin Endocrinol Metab 79, 1525-9 (1994); Bleyer, W. A., CA Cancer J Clin 40, 355-67 (1990); Reijo, R. et al. Nat. Genet. 10, 383-93 (1995); Oates et al., Hum Reprod 17, 2813-24 (2002). In fact, this is true in numerous cases, as such de novo mutations account for several types of male-factor infertility already defined at a genetic level and increasing numbers of males are left infertile during their childhood by cancer chemotherapy. See Sadeghi-Nejad, et al., Urol J 4, 192-206 (2007); Reijo et al. Nat. Genet. 10, 383-93 (1995); Bleyer et al., CA Cancer J Clin 40, 355-67 (1990); Oates et al., Hum Reprod 17, 2813-24 (2002); Bhasin, S., J Clin Endocrinol Metab 92, 1995-2004 (2007); and Geens, M. et al., Hum Reprod Update 14, 121-30 (2008). As a new hope for many infertile men with azoospermia, a pioneering breakthrough in stem cell biology that manifested strong links between reproductive biology and genetic research was the discovery that mouse testes contained spermatogonial stem cells capable of generating fully functional sperm following isolation and transplantation into testes of another mouse. See Brinster & Zimmermann, Proc Natl Acad Sci USA 91, 11298-302 (1994). Similar experiments soon followed in rats, and isolated mouse spermatogonia were next shown to maintain their regenerative potential after months in culture. See Clouthier et al., Nature 381, 418-21 (1996); Nagano et al., Tissue Cell 30, 389-97 (1998). New culture media supporting the long term proliferation of rodent spermatogonial lines in vitro have since been formulated and scientists are now on the brink of establishing conditions required to cultivate human spermatogonial lines from testis biopsies. See Kanatsu-Shinohara et al., Biol Reprod 69, 612-6 (2003); Hamra, F. K. et al., Proc Natl Acad Sci USA 102, 17430-5 (2005); Conrad, S. et al. Nature (2008); and Kossack, N. et al. "Isolation and Characterization of Pluripotent Human Spermatogonial Stem Cell-Derived Cells." Stem Cells (2008). Ostensibly, the ability to propagate spermatogonial lines in culture, prior to using them to produce functional spermatozoa by transplanting them back into the testes of their own donor, presents a clear strategy to cure many existing types of male infertility. Due in large part to the multipotent nature of germline stem cells however, before these breakthroughs are translated into practice it is imperative that preclinical details of such cellular therapies first be stringently evaluated in more advanced, non-human recipients of medical relevance. See Geens, M. et al., Hum Reprod Update 14, 121-30 (2008); Conrad, S. et al. "Generation of pluripotent stem cells from adult human testis." Nature (2008); Kossack, N. et al. "Isolation and Characterization of Pluripotent Human Spermatogonial Stem Cell-Derived Cells." Stem Cells (2008); Hermann, B. P. et al. Stem Cells 25, 2330-8 (2007); and Zhang et al., J Cell Physiol 211, 149-58 (2007).

Kits

The invention includes various kits which comprise a feeder free culture system for the maintenance or proliferation of at least one SSC. Although exemplary kits are described below, the contents of other useful kits will be apparent to the skilled artisan in light of the present disclosure. Each of these kits is included within the invention.

In one aspect, the invention features a kit for maintaining at least one SSC in a feeder-free culture system, comprising a culture system comprising serum-free defined culture medium and pre-conditioning feeder cells from one or more proprietary cell lines including cell in BEF1 and cell line BSC1, an applicator, and instructional material, wherein the instructional material comprises instructions for the use of the kit to maintain at least one SSC in the feeder-free culture system. In another aspect, the invention features a kit for proliferating at least one SSC in a feeder-free culture system, comprising a culture system comprising serum-free defined culture medium and preconditioning feeder cells, or media that has already been pre-conditioned, an applicator, and instructional material, wherein the instructional material comprises instructions for the use of the kit to proliferate at least one SSC in the feeder-free culture system.

The invention also features a kit for administering a population of enriched SSCs to a mammal, comprising a culture system comprising feeder-free defined culture medium preconditioned with feeder cells, an applicator, and instructional material, wherein the instructional material includes instructions for the use of the kit to proliferate at least one SSC in the feeder-free culture system and for the applicator-based administration of the enriched SSCs to a mammal.

The particular applicator included in the kit will depend on, e.g., the method and/or the composition used to introduce a population of enriched SSCs to a cell. Such applicators are well-known in the art and may include, among other things, a membrane, an implant, a syringe, and the like. Moreover, the kit comprises an instructional material for the use of the kit. These instructions simply embody the disclosure provided herein.

The kit may also include a pharmaceutically-acceptable carrier. The composition is provided in an appropriate amount as set forth elsewhere herein. Further, the route of administration includes, but should not be limited to, direct contact with the desired site of administration, as well as contact with a cell or tissue adjacent to the desired site of administration.

Compositions and methods for the isolation, purification, enrichment, proliferation and maintenance of SSC, as encompassed by the kits of the invention, are described in detail elsewhere herein.

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

EXAMPLES

Isolation and Culture of Bovine or Porcine Undifferentiated Spermatogonia

1. Prepare collagenase/DNase incubation solution (1-5 mg/ml collagenase, Worthington Biological and 5-10 mg/ml DNase, Sigma-Aldrich).
2. Manually tease apart 100-200 mg of dissected bovine or porcine testicular parenchyma using micro forceps and place into collagenase/DNase digestion solution.
3. Incubate at 37° C. with gentle swirling at a periodic interval until seminiferous tubules have separated.
4. Allow seminiferous tubule fragments to settle on ice, remove supernatant and wash in Hanks Balanced Salt Solution available from Life Technologies, Inc., Carlsbad, Calif. 92008 USA, (HBSS) or suitable physiological buffer. Repeat procedure until supernatant is relatively clear.
6. After last settling incubation, remove supernatant and re-suspend tubules in trypsin/DNase digestion buffer (Invitrogen).
7. Incubate at 37° C. and then add more DNase solution followed by pipetting to make a single cell suspension consisting of germ cells and Sertoli cells.
8. Add fetal bovine serum or other suitable protein source to stop trypsin digestion and pass the cell suspension through a suitable cell strainer to remove tissue fragments thereby yielding a single cell suspension.
9. Centrifuge at 600×g for 7 min at 4° C. to pellet cells.
10. Aspirate supernatant and re-suspend cells in DPBS-S (Phosphate buffered saline with 1% FBS, 10 mM Hepes, 1 mM Pyruvate, 1 mg/ml glucose, $1 \times 10^4$ u/ml penicillin, $1 \times 10^4$ μg/ml Streptomycin) or other suitable physiological buffer.
11. Overlay cell suspension onto 30% percoll solution at a density of 2 ml percoll solution per 5 ml cell suspension. Other volumes and ratios of percoll and cell suspension may also be suitable.
12. Centrifuge at 600×g for 8 min at 4° C.
13. Remove supernatant to recover cell pellet and re-suspend in DPBS-S or other suitable buffer.
14. Centrifuge at 600×g for 7 min at 4° C.
15. Remove supernatant and re-suspend in StemPro culture medium (recipe below).
16. Centrifuge again and wash cells in StemPro to remove residual fetal bovine serum.
17. Re-suspend washed cell pellet in StemPro and add growth factor cocktail (GDNF 40 ng/ml, FGF 10 ng/ml, CSF-1 10 ng/ml, SDF-1 10 ng/ml). Other concentrations of these growth factors may be suitable.
18. Add cells to 6-well culture plates pre-coated with 0.1% gelatin at a density of $2 \times 10^6$ cells per well and incubate overnight at 37° C. Other culture plate formats, gelatin concentrations, and cell densites may be suitable.
19. Next day, add HBSS or other suitable physiological buffer to each well and gently pipette throughout the well to remove non adherent cells.
20. Collect suspension of non-adherent cells which is enriched for bovine spermatogonia.
21. Centrifuge the germ cells at 600×g for 7 min at 4° C., remove the supernatant and re-suspend in BEF1 or BSC1 feeder cell conditioned StemPro media and add growth factor cocktail.
22. Place cells into 24-well plates pre-coated with Matrigel (BD Biosciences). Other substrates such as Laminin and Fibronectin may also be suitable for coating of plastic culture wells and other culture plate formats including 96-well, 48-well, and 12-well may be suitable.
23. Incubate cells at 37° C. in an atmosphere of 5% $CO_2$ in air. BEF1 or BSC1 preconditioned media is changed every other day and cells are re-plated onto new matrix coated plastic plates at an interval of 7-10 days.

The cells can be maintained in these conditions for greater than 6 months and form clumps with morphology as shown in FIG. 1. In addition, the cells retain expression of molecular makers of undifferentiated spermatogonia including the transcription factor PLZF.

Preconditioning of StemPro Media

1. Maintain BEF and BSC feeders in Dulbecco's Modified Eagle Medium (DMEM) growth media commercially available from Life Technologies, Inc., Carlsbad, Calif. 92008 USA and sub-culture 1:2-1:5 at 80% confluence.
2. Preconditioning of StemPro occurs 24 hr prior to adding the media to cultured spermatogonia.
3. Remove DMEM growth media and wash cells with HBSS or other suitable physiological buffer and discard.
4. Add StemPro media to feeders and incubate at 37° C. overnight.
5. Collect precondition StemPro media and filter through 0.45 μm syringe filter, add growth factor cocktail (GDNF, FGF2, CSF-1, and SDF-1).
6. Add to bovine spermatogonia being maintained in plastic culture wells coated with Matrigel or other suitable matrices.

Creation of Bovine Embryonic Fibroblast (BEF) Feeders

1. Collect a 35 day old bovine embryo into PBS.
2. Remove head and visceral organs including the gonads.

3. Dice embryo into small sections with a sterile razor blade.
4. Digest the tissue in trypsin solution by incubation at 37° C.
5. Allow tissue to settle on ice then pipette vigorously.
6. Add more trypsin solution and incubate at 37° C.
7. Allow tissue to settle on ice, collect supernatant and centrifuge at 300×g for 5 min.
8. Re-suspend pelleted cells in DMEM growth media and place in culture plates.
9. Grow cells at 37° C. in an atmosphere of 5% $CO_2$ in air.
10. Immortalize cells by transfecting with a recombinant DNA construct for overexpression of telomerase.

Creation of Bovine Somatic Cell (BSC) Feeders

1. Bovine testis cells that adhere to gelatin coated culture wells during the differential plating procedure for isolation of spermatogonia are maintained in DMEM growth media after the spermatogonia have been removed.
2. This cell population is a mixture of somatic cells from the bovine testis including Sertoli cells, Leydig cells, and fibroblasts.
3. The cells are grown at 37° C. in an atmosphere of 5% $CO_2$ in air and are immortalized by transfection with a recombinant DNA construct for overexpression of telomerase.

| StemPro media for bovine undifferentiated spermatogonia Reagent | Final conc. | Supplier |
| --- | --- | --- |
| DMEM/F12 | | Invitrogen |
| Penicillin & Streptomycin | P: 50 U/ml S: 50 ug/ml | Invitrogen |
| Iron-saturated Transferrin | 10 ug/ml | Sigma |
| $Na_2SeO_3$ | $3 \times 10^{-8}$ M | Sigma |
| 2-ME | 50 uM | Sigma |
| Insulin | 5 ug/ml | Sigma |
| Putrescine | 60 uM | Sigma |
| MEM Non-Essential Amino Acids | 1x | Invitrogen |
| MEM Vitamins | 1x | Invitrogen |
| Fetal Bovine Serum (FBS) | 0.1% | Invitrogen |
| Glutamine | 2 mM | Invitrogen |
| StemPro Supplement | 2% | Invitrogen |

DEPOSITS

A deposit of cell lines BEF1 and BSC1 are and have been maintained by an inventor of the this application, since prior to the filing date of this application. Access to this deposit will be available during the pendency of the application to the Commissioner of Patents and Trademarks and person determined by the Commissioner to be entitled thereto upon request. Upon allowance of any claims in the application, the Applicant(s) will make available to the public without restriction a deposit of each line with the American Type Culture Collection (ATCC), Manassas, Va., 20110. The cell lines deposited with the ATCC will be taken from the same deposit maintained by the inventors and described above. Additionally, Applicant(s) will meet all the requirements of 37 C.F.R. §1.801-1.809, including providing an indication of the viability of the sample when the deposit is made. This deposit of cell lines BEF1 and BSC1 will be maintained in the ATCC Depository, which is a public depository, for a period of 30 years, or 5 years after the most recent request, or for the enforceable life of the patent, whichever is longer, and will be replaced if it ever becomes nonviable during that period. Applicant will impose no restrictions on the availability of the deposited material from the ATCC; however, Applicant has no authority to waive any restrictions imposed by law on the transfer of biological material or its transportation in commerce.

What is claimed is:

1. A method of enriching spermatogonial stem cells (SSCs) from a population of testis-derived cells containing at least one SSC, said method comprising:
    a) providing a media that has been preconditioned with a feeder cell line, wherein said preconditioned media is created by contacting said media with cells, or parts thereof, from the feeder cell line, wherein the feeder cell line is a strain of embryonic fibroblast cells and/or somatic cells isolated from testes;
    b) contacting said population of testis-derived cells with said preconditioned media under conditions suitable for SSC cell maintenance and enrichment.
2. The method of claim 1 wherein said feeder cell line is bovine.
3. The method of claim 2 wherein said feeder cell line strain is selected from the group consisting of cell line BEF1 and cell line BSC1.
4. The method of claim 2 wherein preconditioning includes the steps of: a) contacting media with feeder cells selected from the group consisting of bovine embryonic fibroblast cells and/or bovine testicular somatic cells; b) allowing said cells to reproduce on said media; and thereafter c) removing said feeder cells.
5. The method of claim 4 wherein said cell feeder cells are derived from cell line BEF1 and/or BSC1.
6. The method of claim 1 wherein said SSC are bovine cells.
7. A method of isolating spermatogonial stem cells from bovine testicular tissue comprising:
    a. Obtaining testicular tissue from a subject
    b. Incubating said tissue with collagenase to separate spermatogonia and Sertoli cells
    c. Separating tubules from other cell types
    d. Digesting tubules with trypsin to yield a suspension spermatogonial cells and Sertoli cells and
    e. Separating the spermatogonial cells and Sertoli cells from said suspension.
8. The method of claim 7 wherein said separating of tubules from other cell types is by gravity sedimentation.
9. The method of claim 7 wherein said separating of spermatogonial cells and Sertoli cell from said suspension is by centrifugation and incubation on culture dishes to which sertoli cells preferentially bind.
10. The method of claim 1 wherein said pre-conditioned media is DMEM/F12 media.
11. The method of claim 1 wherein said media is supplemented with serum replacement supplement.
12. The method of claim 10 wherein said serum replacement supplement is StemPro.
13. A media for maintenance and enrichment of bovine spermatogonial stem cells created by the method of claim 1.
14. The media of claim 13 wherein said media is comprised within plastic culture wells pre-coated with Matrigel.
15. A population of enriched spermatogonial stem cells created by the method of claim 1.
16. The population of cells of claim 15, wherein said cells are bovine cells.
17. A method of generating at least one mammal progeny, said method comprising:

a) administering a population enriched SSCs produced by the method of claim 1 to a testis of a male recipient mammal wherein feeder cells do not need to be removed from said population;
b) allowing said enriched SSCs to generate a colony of spermatogenesis in said recipient mammal; and
c) mating said recipient mammal with a female mammal of the same species as said recipient mammal.

* * * * *